(12) United States Patent
Philips

(10) Patent No.: US 8,910,867 B2
(45) Date of Patent: Dec. 16, 2014

(54) SYSTEM AND METHOD FOR CARD QUALITY ASSURANCE

(75) Inventor: Simon Edward Philips, York (GB)

(73) Assignee: Mastercard International Incorporated, Purchase, NY (US)

( * ) Notice: Subject to any disclaimer, the term of this patent is extended or adjusted under 35 U.S.C. 154(b) by 368 days.

(21) Appl. No.: 11/865,830

(22) Filed: Oct. 2, 2007

(65) Prior Publication Data

US 2008/0152874 A1  Jun. 26, 2008

Related U.S. Application Data

(63) Continuation of application No. PCT/US2006/012289, filed on Apr. 4, 2006.

(60) Provisional application No. 60/668,306, filed on Apr. 4, 2005.

(51) Int. Cl.
*G06K 7/00* (2006.01)
*G01N 21/88* (2006.01)

(52) U.S. Cl.
CPC .................... *G01N 21/88* (2013.01)
USPC .......................... 235/438; 235/492

(58) Field of Classification Search
USPC ................................. 235/438, 492
See application file for complete search history.

(56) References Cited

U.S. PATENT DOCUMENTS

| | | | |
|---|---|---|---|
| 5,714,743 A * | 2/1998 | Chiba et al. | 235/449 |
| 6,170,752 B1 | 1/2001 | Miller | |
| 6,191,850 B1 * | 2/2001 | Chiang | 356/237.4 |
| 6,394,346 B1 * | 5/2002 | Bonneau et al. | 235/438 |
| 6,407,404 B1 | 6/2002 | Yokoyama et al. | |
| 2004/0011876 A1 * | 1/2004 | Schmuck et al. | 235/492 |

FOREIGN PATENT DOCUMENTS

| | | |
|---|---|---|
| JP | 11154201 | 6/1999 |
| JP | 2001203855 | 7/2001 |

* cited by examiner

*Primary Examiner* — Kristy A Haupt
(74) *Attorney, Agent, or Firm* — Baker Botts L.L.P.

(57) ABSTRACT

A system and method for payment card quality assurance is provided. The system and method use a grid or similar graphic to optically accentuate card surface deformations in test cards. The grid enables a generic test that checks the quality across the whole card surface. Process card monitors with the grid pattern can be used to qualify card-manufacturing processes.

12 Claims, 4 Drawing Sheets

Card print graphic

Card print graphic

| e1 | Distance from the left edge of the card to the left edge of the antenna exclusion area | 6.13+[2.54] |
|---|---|---|
| e*1 | Id, first character of Name and address area not printed | 8.67 |
| e2 | Distance from the left edge of the card to the right edge of the antenna exclusion area | 76.50 |

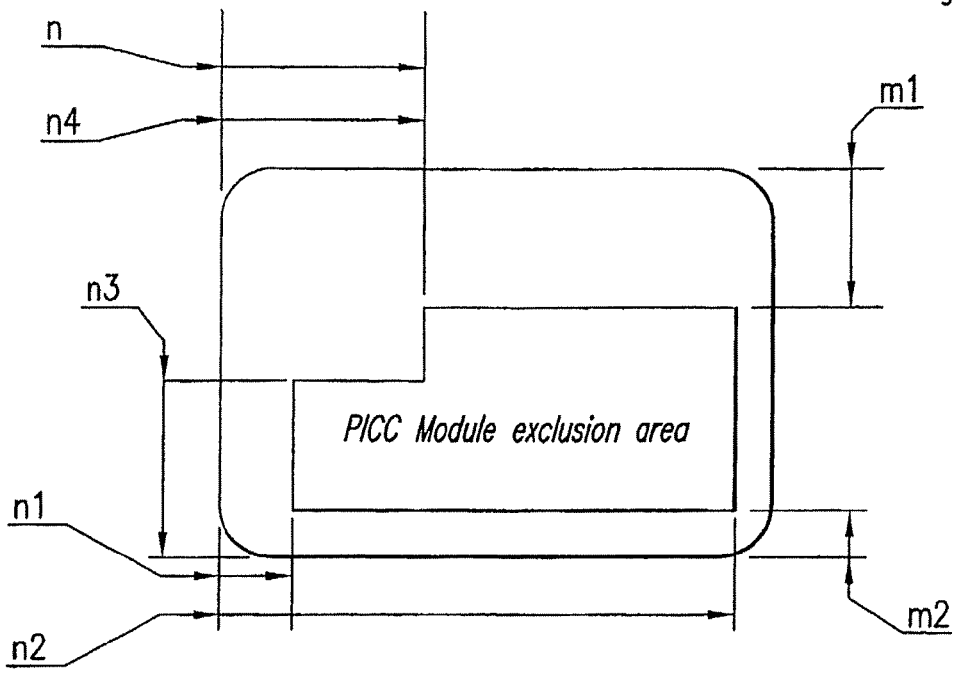

Forbidden zone for the module
The module shall not enter the area indicated in the drawing.

| m1 | Distance from the top of the card to the top of the PICC module exclusion area | 18.79 | maxi |
|---|---|---|---|
| m2 | Distance from the bottom of the card to the bottom of the PICC module exclusion are [3 lines embossed on the address area] | 6..04 | maxi |
| m*2 | Distance from the bottom of the card to the bottom of the PICC module exclusion are [2 lines embossed on the address area] | 6..04 | maxi |
| n1 | Distance from the left edge of the card to the left edge of the PICC module extension area | 9.63 | maxi |
| n2 | Distance from the left edge of the card to the right edge of the PICC module extension area | 5..15 | maxi |
| n3 | Height definition of the ICC Contact area available for PICC module location | 82..12 | mini |
| n4 | Width definition of the ICC Contact area available for PICC module location | 24.03 | mini |
| p | Reverse side: Distance from the right edge of the signature panel to the right edge of the card | 25..00 | mini |

FIG.3

Test Layout

PICC Module exclusion area

Antenna exclusion area

Printing:
Background: half millimetric grid, black printing
Module exclusion area: over printing in solid red
Antenna exclusion area: over printing in solid blue

SYSTEM AND METHOD FOR CARD QUALITY ASSURANCE

CROSS-REFERENCE TO RELATED APPLICATION

This application is a continuation of International Application PCT/US06/012289, filed Apr. 4, 2006, which claims the benefit of U.S. provisional patent application No. 60/668,306 filed on Apr. 4, 2005, each of which is incorporated by reference in its entirety herein.

BACKGROUND OF THE INVENTION

A "smart" payment card is a type of plastic card embedded with a computer chip that stores and transacts data between users. The computer chip includes a microprocessor and memory, or only a memory chip with non-programmable logic. The data is associated with either value or information or both and is stored and processed within the card's chip. The card data is transacted via a reader that is part of a computing system. It can contain more data than a magnetic stripe card and can be programmed to reveal only the relevant information. For example, it could tell a device in a store that there is sufficient balance in an account to pay for a transaction without revealing the balance amount. Encryption techniques secure the data, and the processor allows it to be programmed for different applications. Smart cards are now widely deployed, for example, in healthcare, banking, entertainment and transportation industries. There are two general categories of smart cards: contact and contactless smart cards. A contact smart card requires insertion into a smart card reader with a direct connection to a conductive micromodule on the surface of the card. It is via these physical contact points, that transmission of commands, data, and card status takes place. A contactless card requires only close proximity to a reader. Both the reader and the card have matching radiofrequency antennas providing a contactless electromagnetic link by which the two can communicate.

The smart cards are fabricated, for example, by embedding a micro module into the plastic substrate or card. Contactless smart cards may be fabricated by laminating the antenna/chip module between top and bottom card layers. The antenna is typically 3-5 turns of very thin wire or conductive ink connected to the contactless chip.

The industrial fabrication and the properties of smart cards are subject to voluntary industry standards. A basic smart card standard is the ISO 7816 series, part 1-10. These standards are derived from the financial ID card standards and detail the physical, electrical, mechanical, and application programming interface to a contact chip card. For example, the ISO 7816-1 Standard limits the physical size of the card. The card is the ID-1 size: (85.6 mm×54.0 mm×76 mm). This is the same size as a bank credit card. The standard includes accommodation of exposure limits for a number of electromagnetic phenomena such as X-rays, UV light, electromagnetic fields, static electrical fields, and ambient temperature of the card. Furthermore, ISO 7816-1 defines the mechanical characteristics of a card (e.g., when it is bent or flexed) to make sure that plastic cards with embedded chips and antennas are manufactured in a way that guarantees flawless operation over the expected lifetime of a card.

Smart cards deployed, for example, in the payment-by-card industry, also may include features such as magnetic stripes and embossed lettering, so that the cards are operable with legacy payment infrastructure such as magnetic stripe card readers and embossed card paper imprinters that are still in use in the field. Embossing allows for textual information or designs on the card to be transferred to paper by using a simple and inexpensive device. ISO 7811 specifies the embossed marks, covering their form, size, embossing height, and positioning. Use of magnetic stripe technology advantageously reduces the flood of paper documents associated with embossing. ISO 7811 also specifies the properties of the magnetic stripe, coding techniques, and positioning.

The smart cards, may be fabricated by laminating a foil or inlay, which, for example, supports a chip and antenna, into a PVC plastic card. A laminating press may be used adjust the pressure applied to the cards. Too much pressure on a contactless inlay can break the antenna, rendering the contactless feature useless.

Consideration is now being given to ways of providing solutions for improving card fabrication. Attention is directed to reducing variations in the physical properties of the cards consistent with commonly accepted standards. In particular, attention is directed to improving standard compliance procedures.

SUMMARY OF THE INVENTION

The invention provides a system and method for payment card quality assurance. The system and method use a grid or similar graphic to optically accentuate card surface feature or deformations. The system and method may be used to qualify card-manufacturing processes. The invention allows for identification, prior to volume manufacture, of a deformation in the card that may result in unacceptable quality cards.

The grid or similar graphic enables a generic test that checks the quality across the whole card. This whole card testing can replace multiple tests for each card specific graphic, thus reducing testing time and costs.

Further features of the invention, its nature and various advantages will be more apparent from the accompanying drawings and the following detailed description.

BRIEF DESCRIPTION OF THE DRAWINGS

FIGS. 2 and 3 are schematic illustrations of the specification parameters for the geometrical location of the antenna and the PICC module in a contactless payment card, respectively.

DETAILED DESCRIPTION OF THE INVENTION

Figure 1:
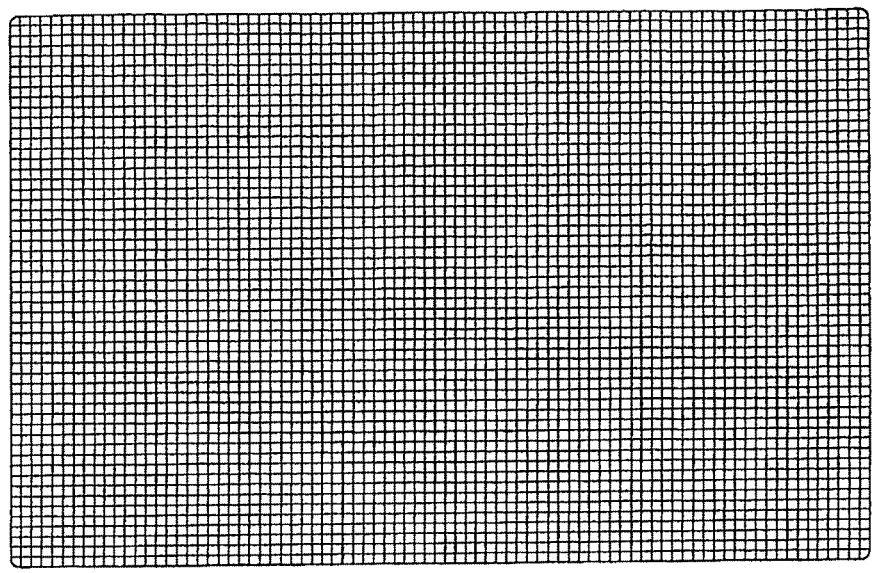
FIG. 1 is a schematic illustration of payment card and a grid pattern that accentuates surface features of the card, in accordance with the principles of the present invention. The payment card may be standard size (e.g., ID-1 size). The grid dimensions may be about half a millimeter or less.

The present invention provides a system and method for payment card quality assurance (QA). This system and method employ a grid pattern or similar pattern, which optically amplifies or accentuates surface features, for the inspecting the surfaces of product payment cards. FIG. 1 shows an exemplary grid pattern 110. Grid pattern 110 preferably blankets the entire card surface, which allows the entire card surface to be inspected for defects or deformation quickly, for example, in plan view.

The grid pattern may be designed to exploit diffraction, lenticular, or other optical phenomena for amplification of the surface features. The grid pattern may be applied to the surfaces of the subject test cards using an adhesive tape or sticker. Alternatively the grid-like pattern may be generated by optical elements (e.g., screens) in a plan view optical inspection system.

In an exemplary application of the invention, process monitor cards are processed through same fabrication steps used for product payment cards. (See e.g. FIG. 1, process monitor card 100). The process monitor cards are fabricated to have a surface grid pattern 110 or similar pattern, which optically amplifies surface features. The grid pattern or other similar pattern makes plan view inspection of surface defects easier. The process monitor cards may be used to qualify the fabrication process to ensure that the product payment cards fabricated by the process are in compliance with standard industry or any other desired product specifications.

An exemplary application of the inventive QA system and method is described herein with reference to the manufacture of contactless or proximity-only payment cards that are fabricated by laminating an inlay together with plastic sheets. The process monitor cards may be fabricated, for example, by using a plastic sheet that has a printed or built in grid pattern as an overlay sheet in the laminate.

The inlay, which may be a discrete or virtual layer inside the payment card, carries an antenna and the integrated circuit module (PICC). The design of the inlay may be according to ID-1 specifications. A product specification may, for example, define acceptable card thickness outside embossed areas and add-on areas. The thickness of the inlay is such that it allows the generation of a card within a defined product specification.

Figure 2:
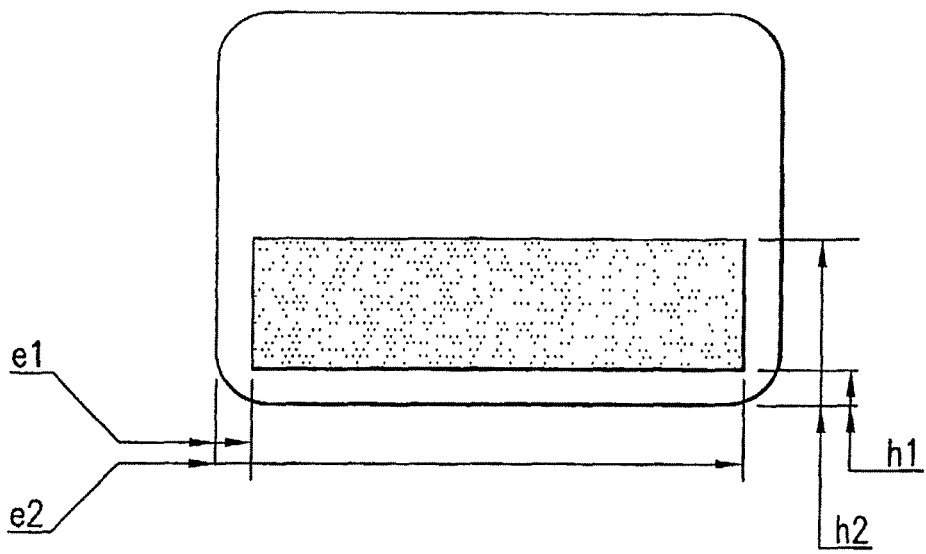

The antenna and the PICC are geometrically laid out to avoid card areas that are designated for other card features, such as embossed characters, holograms, magnetic stripes, etc. FIGS. 2 and 3 show graphically the specification parameters for the location of the antenna and the PICC module, respectively. With reference to these figures, Tables II and II show exemplary values for the specification parameters for the antenna and PICC module layout respectively.

TABLE I

Layout Specifications for Antenna Exclusion Area

| e1 | Distance from the left edge of the card to the left edge of the antenna exclusion area | 6.13+ (2.54*n] | 6.13 |
|---|---|---|---|
| e'1 | Id, first character of Name and address area not printed | 8.67 | 8.67 |
| e2 | Distance from the left edge of the card to the right edge of the antenna exclusion area | 76.50 | 8.9 |
| h1 | Distance from the bottom of the card to the bottom edge of the antenna exclusion area | 24.03 | ns |
| h2 | Distance from the bottom of the card to the top edge of the antenna exclusion area (fourth line shall not be used)r | 6.04 | 6.04 |
| h'2 | Distance from the bottom of the card to the top edge of the antenna exclusion area (third and fourth lines shall not be used)r | 9.63 | 9.63 |

TABLE II

Layout Specifications for PICC Exclusion Area

| m1 | Distance from the top of the card to the top of the PICC module exclusion area | 18.79 maxi |
|---|---|---|
| m2 | Distance from the bottom of the card to the bottom of the PICC module exclusion area [3 lines embossed on the address area] | 6.04 maxi |
| m'2 | Distance from the bottom of the card to the bottom of the PICC module exclusion area [2 lines embossed on the address area] | 9.63 maxi |
| n1 | Distance from the left edge of the card to the left edge of the PICC module exclusion area | 5.15 maxi |
| n2 | Distance from the left edge of the card to the right edge of the PICC module exclusion area | 82.12 mini |
| n3 | Height definition of the ICC Contact area available for PICC module location | 24.03 mini |
| n4 | Width definition of the ICC Contact area available for PICC module location | 25.00 mini |
| p | Reverse side: Distance from the right edge of the signature panel to the right edge of the card | 25.00 mini | where m1 => ICC contact area;
m2 => embossing area;
n1 => ICC contact area;
n2 => hologram;
n3 => embossing area; and
n4 => ICC contact area The product specification may require that the layout appearing on the product payment card should deviate laterally by no more than 0.1 mm as measured against the original image through an optical or electronic device with a magnification of at least 10 times.

Figure 4:
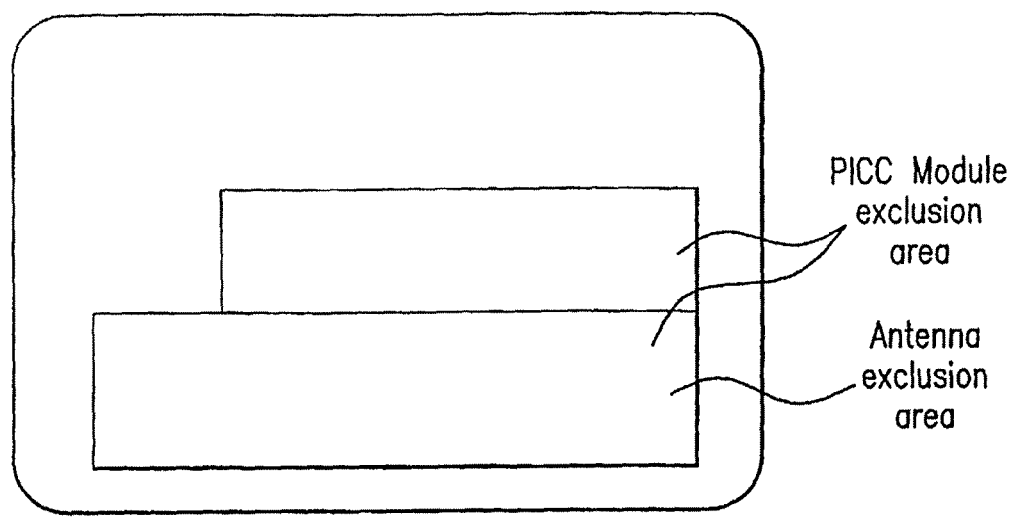
FIG. 4 is an illustration of an exemplary process monitor card fabricated with a grid pattern, which has a spacing of about half a millimeter, for inspecting compliance with inlay layout specifications, in accordance with the principles of the present invention.

In accordance with the invention, the card fabrication process may be qualified by testing process monitor cards. The process monitor cards for quality assurance may be fabricated, for example, by using a plastic sheet, which has a printed or built in grid pattern, as an overlay sheet in the laminate. FIG. 4 shows an exemplary process monitor card fabricated with a plastic sheet having a grid pattern for inspecting compliance with the inlay layout specification. The grid pattern has a suitable spacing (e.g., about half a millimeter).

Other card features, such as embossed characters, holograms, magnetic stripes, etc., are constructed at later or "personalization" steps in the card manufacturing process. These card features or characteristics are also subject to the product specifications. Table III and IV show exemplary product specifications for the surface profile of the magnetic stripe, and for card surface irregularity and roughness. Quality assurance procedures for these features also may be advantageously based on process monitor cards, which have grid patterns on their surfaces to amplify or accentuate the surface features.

TABLE III

Surface Profile of the Magnetic Stripe

| Surface | Stripe Width and surrounding | Vertical deviation* | Standard |
|---|---|---|---|
| Profile type; Mag area convex id | W = 6.35 mm (track 1 & 2) | A < 9.5 µm | ISO 7811-6 |
| | W = 10.28 mm (tracks 1, 2 & 3) | A < 15.4 µm | |
| Profile type; Mag area concave id | W = 6.35 mm | A < 5.8 µm | ISO7811-6 |
| | W = 10.28 mm | A < 9.3 µm | |
| Adjacent surface | Surface of the stripe to adjacent surface | −5 µm < h < 38 µm | ISO 7811-6 |
| Surrounding | No surface distortion, s, measured from the top of the card | 19.05 > s > 2.54 mm | XYZ . . . |

*The vertical deviation measured on the transverse surface profile of the magnetic stripe

TABLE IV

Surface Irregularity and Roughness

| Surface | Irregularities | Surface Roughness | Standard |
|---|---|---|---|
| Front Side | Any surface irregularity due to the antenna and/or module should have height/depth less than 6 mm for a slope (height to length ratio) lower than 1/400. | The surface roughness required for thermal transfer printing is Ra < .025 mm. | XYZ |
| Reverse Side | Any surface irregularity due to the antenna and/or module should have height/depth less than 25 mm for a slope (height to length ratio) lower than 1/25. | | XYZ |

In addition to the desired surface characteristics, payment cards are designed to withstand a number of mechanical stress conditions during their lifetime and to maintain its functionality for the cardholders—at least till their planned expiry dates. The exemplary product card specifications may further include specifications for card characteristics related to mechanical robustness and reliability. The product specification may, for example, specify mechanical or physical characteristics such as bending stiffness, durability, overall card warpage, heat resistance, solidity-peel strength, adhesion or blocking, resistance to surface abrasion, etc. The following mechanical tests are often identified in product specifications as relevant to evaluate the mechanical robustness and reliability of payment cards.

ISO Dynamic Bending Test (2000/4000 cycles).
3-Wheel Test
Wrapping Test
Tensile Stress Test
Corner Impact Test
Vibration Test. (e.g., Standard IEC 68-2-6).
Rotary Impact Test
Combined environmental-mechanical stress test (e.g., temperature-humidity test).

Several of these tests involve visual evaluation of the surface features of the payment card after subjecting the card to mechanical stress. For example, the Vibration Test involves visual inspection to confirm absence of deformation or cracks up on completion of the test protocol. The 3-Wheel and Impact Tests involves visual inspection to of the test card to note appearance of superficial crackles or breaking of the plastic material. It will be readily understood that the process monitor cards fabricated with surface grid patterns to optically amplify or accentuate the surface features of the cards can be advantageously used to simply visual inspection in the aforementioned and other tests.

It will be further understood that the foregoing is only illustrative of the principles of the invention, and that various modifications can be made by those skilled in the art without departing from the scope and spirit of the invention.

What is claimed is:

1. A method for payment card quality assurance, the method comprising:
   fabricating a payment card comprising a surface grid pattern which optically accentuates surface fabrication defects; and
   inspecting the fabricated card surface to detect surface fabrication defects accentuated by the surface grid pattern.

2. The method of claim 1 wherein fabricating a payment card with a surface grid pattern comprises laminating a plastic sheet having a grid pattern.

3. The method of claim 1 wherein the payment card comprises an inlay layer and fabricating the payment card with a surface grid pattern compromises laminating the inlay layer with a plastic sheet having a grid pattern.

4. The method of claim 3, wherein the inlay layer includes an antenna and an integrated circuit module, and wherein inspecting the fabricated card surface for defects and deformations compromises inspecting the geometrical layout of the antenna and the integrated circuit module.

5. The method of claim 1 wherein inspecting the fabricated card surface for defects and deformations comprises inspecting the fabricated card surface visually for surface irregularities and roughness.

6. The method of claim 1 further comprising subjecting the fabricated card to a mechanical stress test, and inspecting the fabricated card surface for defects and deformations after the mechanical stress test.

7. A process monitor card for qualifying a payment card manufacturing process, the process monitor card comprising a surface grid pattern or graphic that optically accentuates surface fabrication defects.

8. The process monitor card of claim 7 comprising a laminated plastic sheet having the grid pattern or graphic.

9. The process monitor card of claim 8 comprising the laminated plastic sheet having the grid pattern or graphic and an inlay layer.

10. The process monitor card of claim 9 wherein the inlay layer includes an antenna and an integrated circuit module.

11. A method for qualifying a payment card manufacturing process, the method comprising;
    fabricating a process monitor card by the payment card manufacturing process, wherein the fabricated process monitor card comprises a surface grid pattern that optically accentuates surface fabrication defects; and
    inspecting the fabricated card surface to determine compliance with payment card product specifications,
    wherein the inspecting comprises detecting surface fabrication defects accentuated by the surface grid pattern.

12. The method of claim 11 further comprising subjecting the fabricated card to a mechanical stress test, and inspecting the fabricated card surface for defects and deformations after the mechanical stress test.

* * * * *